(12) United States Patent
Tanaka et al.

(10) Patent No.: US 7,175,342 B2
(45) Date of Patent: Feb. 13, 2007

(54) SHAFT-MISALIGNMENT-MEASURING DEVICE, A SHAFT-MISALIGNMENT-MEASURING METHOD, A SINGLE-SHAFT COMBINED PLANT USING THE SHAFT-MISALIGNMENT-MEASURING DEVICE AND A START-UP METHOD OF THE SINGLE-SHAFT COMBINED PLANT

(75) Inventors: Satoshi Tanaka, Hyogo-ken (JP); Masamitsu Shimada, Hyogo-ken (JP); Kenyu Takeda, Hyogo-ken (JP); Ryutaro Kitagawa, Hyogo-ken (JP); Fumikatsu Inoue, Hyogo-ken (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 67 days.

(21) Appl. No.: 10/942,133

(22) Filed: Sep. 16, 2004

(65) Prior Publication Data
US 2005/0074049 A1    Apr. 7, 2005

(30) Foreign Application Priority Data
Oct. 1, 2003    (JP)    ............................. 2003-343442

(51) Int. Cl.
G01N 25/00    (2006.01)
G01B 13/19    (2006.01)

(52) U.S. Cl. .......................... 374/55; 33/412; 33/645; 374/45

(58) Field of Classification Search ............... None
See application file for complete search history.

(56) References Cited

U.S. PATENT DOCUMENTS

| | | | | |
|---|---|---|---|---|
| 3,783,522 A | * | 1/1974 | Dodd | ........................... 33/661 |
| 4,033,042 A | * | 7/1977 | Bently | ........................... 33/661 |
| 4,148,013 A | * | 4/1979 | Finn et al. | ............. 340/870.11 |
| 4,161,068 A | * | 7/1979 | McMaster | ..................... 33/412 |
| 4,441,028 A | * | 4/1984 | Lundberg | ..................... 290/52 |
| 4,538,455 A | * | 9/1985 | Klufas | ........................ 73/118.1 |
| 4,586,264 A | * | 5/1986 | Zatezalo | ....................... 33/412 |
| 5,004,084 A | | 4/1991 | Mehr-Ayin et al. | |
| 5,077,905 A | * | 1/1992 | Murray, Jr. | ................... 33/412 |
| 5,222,306 A | * | 6/1993 | Neumann | .................... 33/645 |
| 5,263,261 A | * | 11/1993 | Piety et al. | .................... 33/645 |

(Continued)

FOREIGN PATENT DOCUMENTS

DE    44 26 354 A1    2/1996

(Continued)

OTHER PUBLICATIONS

German Office Action dated Feb. 21, 2006.

*Primary Examiner*—Diego Gutierrez
*Assistant Examiner*—Mirellys Jagan
(74) *Attorney, Agent, or Firm*—Westerman, Hattori, Daniels & Adrian, LLP.

(57) ABSTRACT

In a control equipment 10, shaft-misalignment amount of a shaft 3a of a gas turbine 3 and a shaft 5a of a steam turbine 5 is measured and speed-increase ratio of rotation speed and heat soak time of the steam turbine 5 are set in accordance with the measured shaft-misalignment amount so as to have the shaft-misalignment amount stay within a permissible range when a clutch 7 connects the shafts 3a and 5a.

30 Claims, 7 Drawing Sheets

U.S. PATENT DOCUMENTS

| | | | | |
|---|---|---|---|---|
| 5,514,952 A | * | 5/1996 | Parkinson | 324/207.25 |
| 5,896,672 A | * | 4/1999 | Harris | 33/645 |
| 5,920,999 A | * | 7/1999 | Hutter | 33/645 |
| 6,019,506 A | * | 2/2000 | Senda | 374/55 |
| 6,035,629 A | | 3/2000 | Hilgeman et al. | |
| 6,702,551 B2 | * | 3/2004 | Kikuchi et al. | 415/220 |

FOREIGN PATENT DOCUMENTS

| | | |
|---|---|---|
| DE | 198 29 178 A1 | 1/2000 |
| JP | 10-169407 | 6/1998 |
| JP | 10-184317 | 7/1998 |

* cited by examiner

SHAFT-MISALIGNMENT-MEASURING DEVICE, A SHAFT-MISALIGNMENT-MEASURING METHOD, A SINGLE-SHAFT COMBINED PLANT USING THE SHAFT-MISALIGNMENT-MEASURING DEVICE AND A START-UP METHOD OF THE SINGLE-SHAFT COMBINED PLANT

BACKGROUND OF THE INVENTION

1. Field of the Invention

The present invention is based on the Japanese Patent Application No. 2003-343442 applied on Oct. 1, 2003.

The present invention relates to a shaft-misalignment-measuring device which measures the misalignment of two shafts having a clutch engaged thereto; a shaft-misalignment-measuring method; a single-shaft combined plant employing the shaft-misalignment-measuring device; and a start-up method of the single-shaft combined plant.

2. Description of the Prior Art

In recent years, a single-shaft combined plant having a gas turbine connected directly to a steam turbine with one shaft serves as a combined plant of high efficiency which can flexibly respond to a change of electrical consumption amount per day, emitting a little amount of toxic substances such as NOx. Conventionally, a single-shaft combined plant constructed in the above-mentioned manner actuates a gas turbine and a steam turbine simultaneously. Therefore, in order to start up both turbines simultaneously, a larger start-up torque is required, thereby needing a thyristor that can generate this huge start-up torque.

Additionally, it is necessary to supply cooling steam to the steam turbine so as to prevent the temperature of the steam turbine blades from increasing excessively due to windage loss. However, steam to be supplied to the steam turbine cannot be generated by a heat recovery steam generator which generates steam by using the exhaust gas of a gas turbine until the electrical output of a generator rotated by a gas turbine is increased. Therefore, an auxiliary boiler is necessary which has an enough capacity to supply sufficient cooling steam to the steam turbine. Further, in a conventional single-shaft combined plant, it is necessary to place a gas turbine, a steam turbine and a generator in a line and an axial-flow exhaust type of steam turbine cannot be applied. Therefore, it is necessary to install a condenser under the steam turbine. As a result, it is necessary to install a gas turbine, a steam turbine and a generator on a higher level, which requires a turbine plant building to be constructed so as to have a plurality of floors.

In order to solve these issues, such a single-shaft combined plant as shown in FIG. 11 is proposed that has a clutch 204 applied between a gas turbine 201 and a steam turbine 202. (Refer to the Japanese Patent Application Laid-Open No. 2003-13709.) The single-shaft combined plant shown in FIG. 11 has a generator 203 installed between the gas turbine 201 and the clutch 204. By applying a clutch 204 as described above, it is possible to connect and disconnect a gas turbine 201 and generator 203 and a steam turbine 202. Consequently, at the start-up time, first, only the gas turbine 201 and the generator 203 are started up in a condition that the gas turbine 201 and generator 203 are disconnected from the steam turbine 202 by the clutch 204. Then, when the steam generated in an heat recovery steam generator (not illustrated herein) can be supplied to the steam turbine 202, the steam is introduced into the steam turbine 202 so as to start up the steam turbine 202. After that, when the steam turbine 202 attains the rated rotation speed, the gas turbine 201 and generator 203 will be connected to the steam turbine 202 by the clutch 204, thereby having the torque of the steam turbine 202 transmitted to the generator 203.

Because in a single-shaft combined plant to which this clutch 204 is applied, it is necessary to first start up the gas turbine 201 and the generator 203 only at the beginning of the start-up time, it is possible to make the capacity of a thyristor necessary for start-up small. Also, while only the gas turbine 201 and the generator 203 are being started up, the steam turbine 202 is rotating at a low speed, thereby requiring no cooling steam. As a result, it is possible to make the capacity of an auxiliary boiler small. Additionally, because the thermal expansion of the steam turbine 202 can be absorbed by the clutch 204, it is possible to construct a single-shaft combined plant so as to have a gas turbine 201, a generator 203 and a steam turbine 202 line sequentially in the aforesaid order as shown in FIG. 11, thereby making it possible to place the steam turbine at one end. Consequently, because the steam turbine 202 can be an axial-flow exhaust steam turbine, it is possible to employ an axial-flow exhaust condenser, thereby making it unnecessary to place a turbine shaft on a high level as is conventionally placed.

As described above, because, at the start-up time, a single-shaft combined plant provided with a clutch 204 as shown in FIG. 11 has the steam turbine 202 actuated after the gas turbine 201 is started up, the gas turbine 202 has been rotating at the rated rotation speed for a long time before the start-up of the steam turbine 202. Consequently, the bearing pedestals on the side of the gas-turbine 201 of the clutch 204 are expanded due to high bearing drain oil temperature, whereas the bearing pedestals on the side of the steam turbine 202 of the clutch 204 have a different expansion ratio which depends on the state of the steam turbine 202.

In other words, when the steam turbine 202 is shut down with the condenser vacuum maintained, gland steam is flowing to the bearings of the steam turbine 202 for a long time. As a result, the bearing pedestals on the side of the steam turbine 202 are slightly expanded. However, because the gland steam does not flow to the bearings of the steam turbine 202 when the steam turbine 202 is stopped with the condenser vacuum broken, the bearing pedestals on the side of the steam turbine 202 are approximately in an initial state and are not expanded. Further, because the steam turbine 202 hardly rotates before the steam turbine 202 is started up, the bearing pedestals on the side of the steam turbine 202 do not have such a large expansion ratio as the bearing pedestals on the side of the gas turbine 201.

At the start-up time, in a single-shaft combined plant equipped with a clutch 204 configured as described above, the expansion ratio of the bearing pedestals on the side of the gas turbine 201 differs from the expansion ratio of the bearing pedestals on the side of the steam turbine 202 and this difference in expansion ratio also differs, depending on the state of the steam turbine 202. Further, not only the expansion ratio differs between the bearing pedestals of the gas turbine 201 and the bearing pedestals of the steam turbine 202 but also the lifting amount and the inclination of the shafts of the gas turbine 201 and the steam turbine 202 differ. As a result, there arises a misalignment between the center of the shaft of the gas turbine 201 and the center of the shaft of the steam turbine 202.

The amount of this misalignment between the center of the shaft of the gas turbine 201 and the center of the shaft of the steam turbine 202 gives an influence when the gas turbine 201 and generator 203 are connected to the steam turbine 202 by engaging the clutch 204 at the start-up time.

In other words, because the clutch 204 is engaged in a condition that the gas turbine 201 and generator 203 and the steam turbine 202 are rotating nearly at the rated rotation speed, when the amount of misalignment between the center of the shaft of the gas turbine 201 and the center of the shaft of the steam turbine 202 becomes larger than a predetermined designed value, there is a possibility that an excessive stress is applied to the clutch 204, resulting in a breakage of the clutch 204.

SUMMARY OF THE INVENTION

It is an object of the present invention to provide a shaft-misalignment-measuring device which measures misalignment between two shafts when a clutch is engaged; and a single-shaft combined plant which is eqipped with this shaft-misalignment-measuring device. It is another object of the present invention to provide a start-up method of a single-shaft combined plant which changes over start-up action based on the misalignment between the center position of the steam-turbine shaft and the center position of the gas-turbine shaft at the start-up time.

In order to achieve the above-mentioned objects, according to the present invention, a shaft-misalignment-measuring device is provided with a first temperature sensor which measures the temperature of a first bearing pedestal supporting a first bearing where a first shaft of a first body of revolution is mounted; a second temperature sensor which measures the temperature of a second bearing pedestal supporting a second bearing where a second shaft of a second body of revolution is mounted; and a shaft-misalignment operating section which obtains an expansion amount of the first bearing pedestal from the temperatures measured with the first temperature sensor, obtains an expansion amount of the second bearing pedestal from the temperatures measured with the second temperature sensor and calculates a part of the misalignment amount of the first and the second shafts based on the expansion amounts of the first and the second bearing pedestals.

In a preferred embodiment according to the present invention, a shaft-misalignment-measuring device is provided with a first gap-measuring sensor which measures the dimension to a first fixed point on the upper side of a first shaft of a first body of revolution; a second gap-measuring sensor which measures the dimension to a second fixed point on the lower side of the first shaft on the same plane of the first fixed point; a third gap-measuring sensor which measures the dimension to a third fixed point on the upper side of a second shaft of a second body of revolution; a fourth gap-measuring sensor which measures the dimension to a fourth fixed point on the lower side of the second shaft on the same plane of the third fixed point; and a shaft-misalignment operating section which obtains the inclination of the first shaft from the dimensions to the first and the second fixed points that are measured with the first and the second gap-measuring sensors, respectively, obtains the inclination of the second shaft from the dimensions to the third and the fourth fixed points that are measured with the third and the fourth gap-measuring sensors, respectively, and calculates a part of the misalignment amount of the first and the second shafts, based on the inclinations of the first and the second shafts.

In another preferred embodiment according to the present invention, a shaft-misalignment-measuring device is provided with a plurality of first gap-measuring sensors which are mounted on a plurality of points in the circumferential direction of a first bearing where a first shaft of a first body of revolution is mounted; a plurality of second gap-measuring sensors which are mounted on a plurality of points in the circumferential direction of a second bearing where a second shaft of a second body of revolution is mounted; and a shaft-misalignment operating section which obtains the misalignment of the center of the first shaft from the center of the first bearing based on the dimensions between a plurality of points in the circumferential direction of the first bearing and the first shaft, being measured with the first gap-measuring sensors, obtains the misalignment of the center of the second shaft from the center of the second bearing based on the dimensions between a plurality of points in the circumferential direction of the second bearing and the second shaft being measured with the second gap-measuring sensors and calculates a part of the misalignment amount of the first and the second shafts, based on the misalignment of the centers of the first and the second shafts.

In another preferred embodiment according to the present invention, a shaft-misalignment-measuring method includes a first step, wherein the expansion amount of a first bearing pedestal supporting a first bearing where a first shaft of a first body of revolution is mounted and the expansion amount of a second bearing pedestal supporting a second bearing where a second shaft of a second body of revolution is mounted are obtained; a second step, wherein the misalignment of the center of the first shaft from the center of the first bearing and the misalignment of the center of the second shaft from the center of the second bearing are obtained; a third step, wherein the inclination of the first shaft and the inclination of the second shaft are obtained; and a fourth step, wherein the misalignment amount of the first and the second shafts is obtained, based on the difference in expansion amount between the first and the second bearing pedestals, the difference between the misalignment of the center of the first shaft from the center of the first bearing and the misalignment of the center of the second shaft from the center of the second bearing, and the inclinations of the first and the second shafts.

In another preferred embodiment according to the present invention, a single-shaft combined plant is provided with a gas turbine which serves as a first body of revolution; a steam turbine which serves as a second body of revolution; and a clutch which connects and disconnects a first shaft of the gas turbine and a second shaft of the steam turbine:

wherein, is provided a shaft-misalignment-measuring device which measures the misalignment amount of the first shaft to the second shaft; and wherein, at the start-up time, the speed-increase ratio of the rotation speed of the steam turbine is set based on the misalignment amount of the first shaft and the second shaft beinng measured by the shaft-misalignment-measuring device when the steam turbine is started up with the first and the second shafts disconnected by the clutch after the gas turbine is started up.

In another preferred embodiment according to the present invention, a single-shaft combined plant is provided with a gas turbine which serves as a first body of revolution; a steam turbine which serves as a second body of revolution; and a clutch which connects and disconnects a first shaft of the gas turbine and a second shaft of the steam turbine:

wherein, is provided a shaft-misalignment-measuring device which measures the misalignment amount of the first shaft to the second shaft; and wherein, at the start-up time, the heat soak time of the steam turbine is set based on the misalignment amount of the first shaft and the second shaft being measured by the shaft-misalignment-measuring device when the steam turbine is started up with the first and the second shafts disconnected by the clutch after the gas turbine is started up.

In a further preferred embodiment according to the present invention, a start-up method of a single-shaft combined plant, consisting of a gas turbine which serves as a first body of revolution, a steam turbine which serves as a second body of revolution and a clutch which connects and disconnects a first shaft of the gas turbine and a second shaft of the steam turbine, includes:

a first step, wherein the steam turbine is rotated in a condition that the first shaft and the second shaft are disconnected by the clutch after the gas turbine is rotated;

a second step, wherein the misalignment amount of the first shaft and the second shaft is measured when the steam turbine is started to rotate;

a third step, wherein the speed-increase ratio and the heat soak time of the steam turbine are set in accordance with the shaft-misalignment amount; and a fourth step, wherein the first shaft and the second shaft are connected by the clutch when the rotation speed of the steam turbine is approximately the same as the rotation speed of the gas turbine.

DESCRIPTION OF THE DRAWINGS

This and other objects and features of the present invention will become clear from the following description, taken in conjunction with the preferred embodiments with reference to the accompanying drawings in which.

DESCRIPTION OF THE PREFERRED EMBODIMENTS

Figure 1:
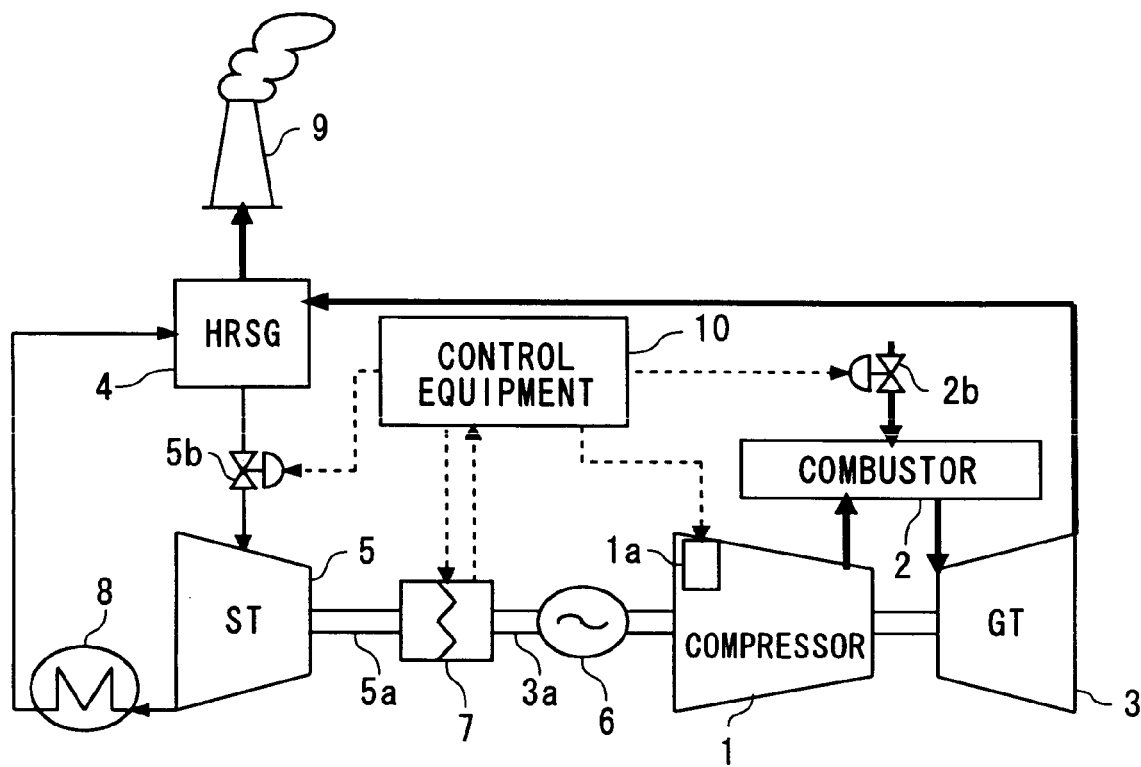
FIG. 1 is a block diagram showing the construction of a single-shaft combined plant in accordance with an embodiment of the prevent invention.

Referring now to the drawings, an embodiment of the present invention will be described hereinafter. FIG. 1 is a block diagram showing the construction of a single-shaft combined plant.

A single-shaft combined plant in FIG. 1 consists of a compressor 1 which compresses the ambient air; a combustor 2 which burns fuel with compressed air from the compressor 1 to supply combustion gas; a gas turbine 3 which is rotated with combustion gas being supplied from the combustor 2: an heat recovery steam generator (HRSG) 4 which generates steam with exhaust gas from the gas turbine 3; a steam turbine 5 which is rotated with steam from the HRSG 4; a generator 6 which is rotated by the gas turbine 3 and the steam turbine 5; a clutch 7 which connects and disconnects a gas-turbine shaft 3a and a steam-turbine shaft 5a; a condenser 8 which recovers steam exhausted from the steam turbine 5 and supplies the recovered steam to the HRSG 4; a chimney 9 which emits exhaust gas from the gas turbine 3 by way of the HRSG 4; and a control equipment 10 which controls action of each block.

The single-shaft combined plant is provided with a fuel-control valve 2b which adjusts the flow rate of fuel being supplied to the combustor 2; a governing valve 5b which controls the supply amount of steam generated in the HRSG 4 to the steam turbine 5; and an inlet guide vane (IGV) 1a which serves as a stationary blade in a first stage of the compressor 1 and adjusts the flow rate of air being supplied to the compressor 1. These fuel-control valve 2b, governing valve 5b and the IGV 1a, respectively, have signals supplied thereto by a control equipment 10, and by having their opening controlled, the rotation speeds of the gas turbine 3 and the steam turbine 5 are controlled. Additionally, the shaft of the compressor 1 and the shaft of the generator 6 are the same shaft 3a shared by the gas turbine 3.

The single-shaft combined plant configured as described above has the steam turbine 5 disconnected until the shaft 3a and the shaft 5a are connected by the clutch 7; and apart from the compressor 1, the gas turbine 3 and the generator 6 that are rotated by the shaft 3a, the steam turbine 5 is rotated by the shaft 5a. Then, when the rotation speeds of the gas turbine 3 and the steam turbine 5 are approximately the same, the clutch 7 automatically gets engaged. When the shaft 3a and the shaft 5a are connected by the clutch 7 in this manner, by the shaft 3a and the shaft 5a that comprise a same shaft, are rotated the compressor 1, the gas turbine 3, the steam turbine 5 and the generator 6, by sharing the same shaft. In acting in the manner as described, when fuel supplied to the combustor 2 is burned by air compressed by the compressor 1, the gas turbine 3 is rotated by using combustion gas from the combustor 2, and concurrently, steam generated by using exhaust gas from the gas turbine 3 in the HRSG 4 is supplied to the steam turbine 5, thereby rotating the steam turbine 5.

1. Measurement of the Shaft-Misalignment

Figure 2:
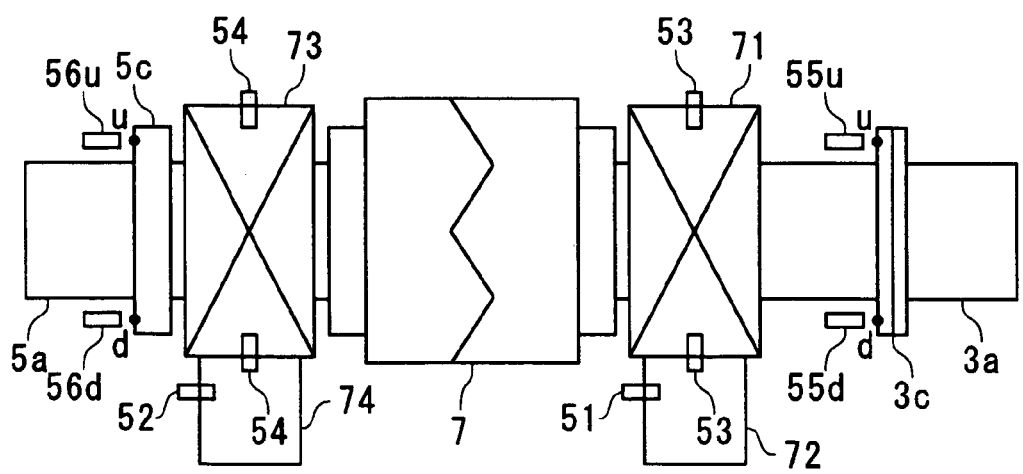
FIG. 2A depicts locations where to install various kinds of sensors constituting a shaft-misalignment-measuring device.

In a single-shaft combined plant constructed as in FIG. 1, a shaft-misalignment-measuring device for measuring the misalignment of the center positions of the shaft 3a and the shaft 5a consists of various kinds of sensors, to be described hereinafter, that are mounted to the surrounding area of the clutch 7 and a shaft-misalignment operating section 101 (FIG. 5) in the control equipment 10. FIG. 2 shows the locations where to install various kinds of sensors which are to be mounted in the surrounding area of the clutch 7.

As shown in FIG. 2, a bearing 71 to which the shaft 3a is mounted and a bearing pedestal 72 supporting the bearing 71 are installed to the clutch 7 on the side of the gas turbine 3, whereas a bearing 73 to which the shaft 5a is mounted and a bearing pedestal 74 supporting the bearing 73 are installed to the clutch 7 on the side of the steam turbine 5. In other words, the construction is to have a clutch 7 installed between the bearings 71 and 73. Further, flanges 3c and 5c are supplied to the shafts 3a and 5a, respectively.

When the clutch 7 and the shafts 3a and 5a are constructed as shown in FIG. 2, temperature sensors 51 and 52 for measuring the temperature of the bearing pedestals 72 and 74, respectively, are mounted to the bearing pedestals 72 and 74, respectively; and gap-measuring sensors 53 and 54 which measure the gaps of the shafts 3a and 5a in the circumferential direction so as to measure the center positions of the shafts 3a and 5a, respectively, are mounted to the bearings 71 and 73, respectively. Additionally, gap-measuring sensors 55u, 55d, 56u and 56d are mounted to the vicinity of the flanges 3c and 5c, respectively, so as to measure the inclination of the shafts 3a and 5a, respectively, by measuring the axial dimensions to the flanges 3c and 5c. At this time, thermocouples, for example, are employed as the temperature sensors 51 and 52. For the gap-measuring sensors 53, 54, 55u, 55d, 56u and 56d, non-contact sensors are applied in order to check the state of the rotating shafts 3a and 5a. For example, eddy-current type of gap sensors or CCD laser sensors are applied.

Having various kinds of sensors mounted as described above, when the temperature of the bearing pedestals 72 and 74, respectively, being measured by the temperature sensors 51 and 52 is supplied to the shaft-misalignment operating section 101, the expansion amount of the bearing pedestals 72 and 74, respectively, is obtained. Namely, when the temperature Ti1 of the bearing pedestal 72 is measured by the temperature sensor 51 and when the temperature Ti2 of the bearing pedestal 74 is measured by the temperature sensor 52, the expansion amount $\Delta$hi1 of the bearing pedestal 72 is obtained from the formula (1), and the expansion amount $\Delta$hi2 of the bearing pedestal 74 is obtained from the formula (2); where h0 is the height of the bearing pedestals 72 and 74; $\tau$ is the linear expansion factor; To1 is the temperature (offset temperature) when the bearing pedestal 72 is installed; and To2 is the temperature (offset temperature) when the bearing pedestal 74 is installed.

$$\Delta hi1 = h0 \times \tau \times (Ti1 - To1) \tag{1}$$

$$\Delta hi2 = h0 \times \tau \times (Ti2 - To2) \tag{2}$$

Figure 3A:
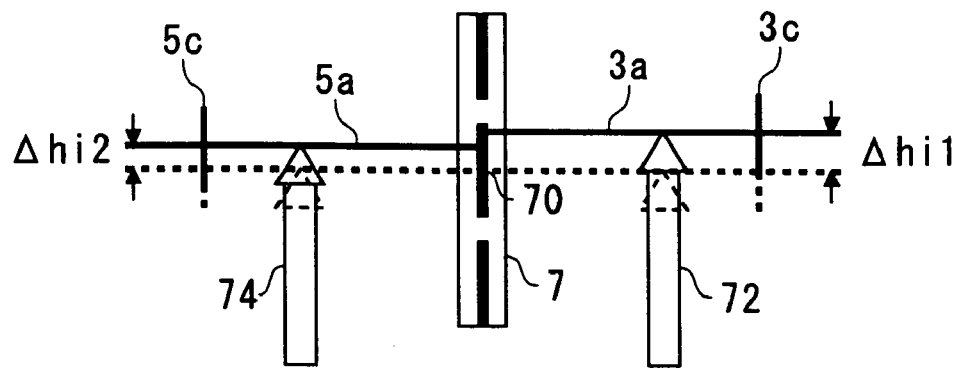
FIGS. 3A through 3C are schematic drawings showing a shaft-misalignment condition of a steam turbine and a gas turbine.
Figure 3B:
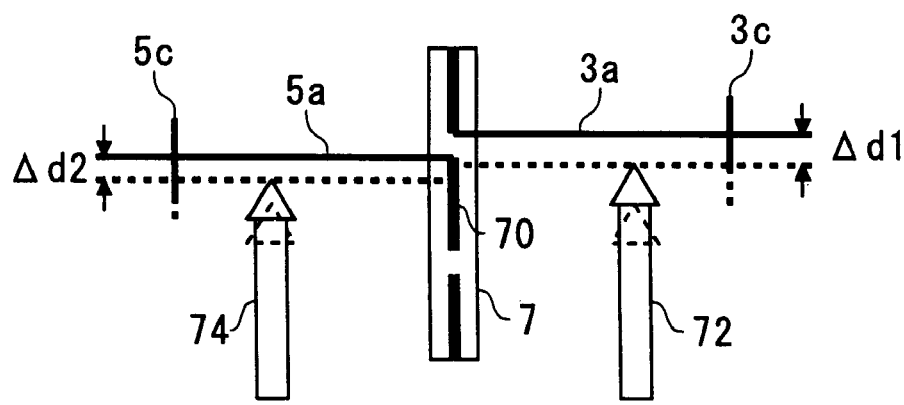
Figure 3C:
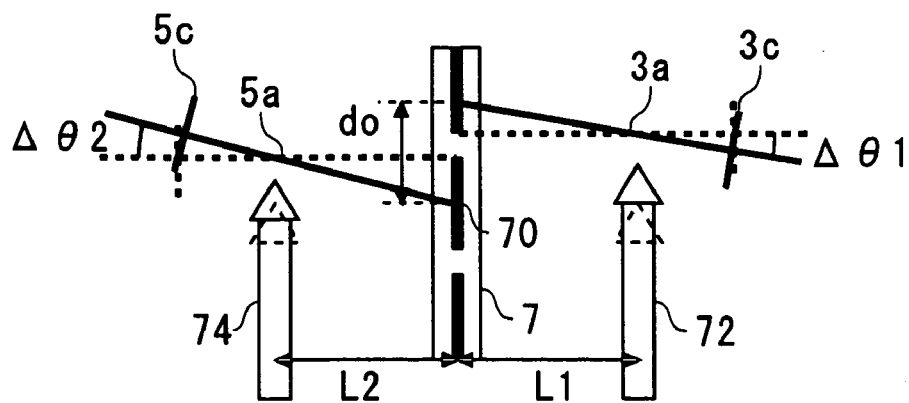

By calculating the measurements of the temperature sensor 51 by the shaft-misalignment operating section 101 as described above, it is confirmed, as shown in FIG. 3A, that the height of the bearing pedestal 72 supporting the shaft 3a is expanded for $\Delta$hi1. Also, by calculating the measurements of the temperature sensor 52 by the shaft-misalignment operating section 101, it is confirmed, as shown in FIG. 3A, that the height of the bearing pedestal 74 supporting the shaft 5a is expanded for $\Delta$hi2. FIG. 3A through FIG. 3C are schematic drawings showing the misalignment state of the shafts 3a and 5a.

Figure 4:
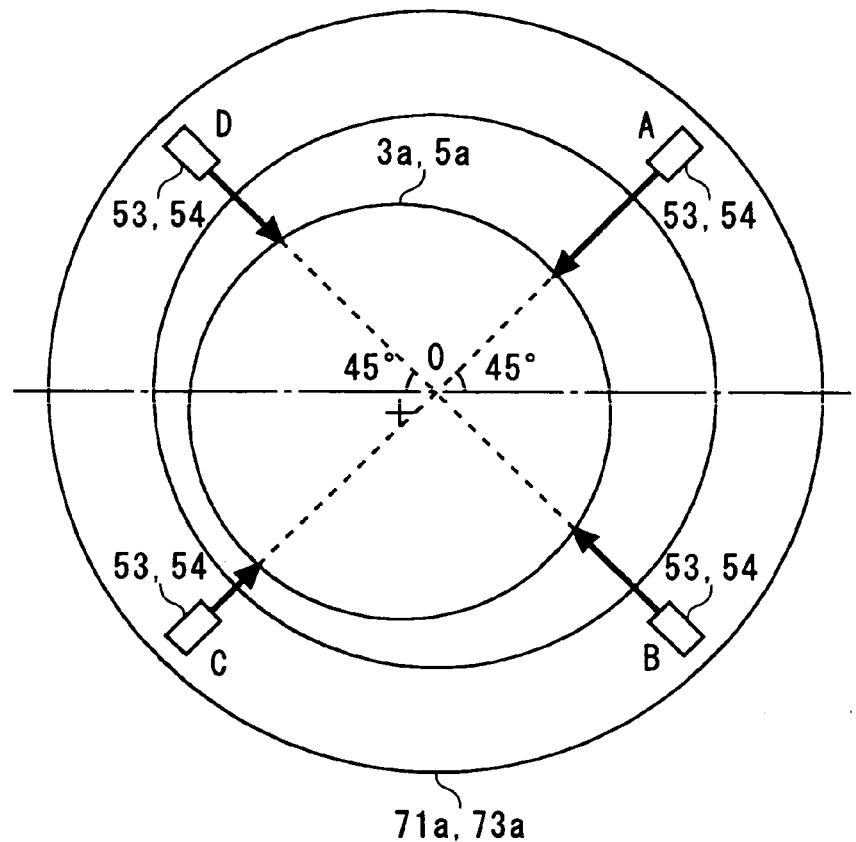
FIG. 4 depicts locations on a bearing where to install gap-measuring sensors.

Further, as shown in FIG. 4, the gap-measuring sensors 53 and 54 to be mounted to the bearings 71 and 73 are installed at four points A through D in the circumferential direction of bearing support rings 71a and 73a being provided to the bearings 71 and 73. Here, the straight line connecting the centers O of the bearing support rings 71a and 73a to the four points A through D, respectively, forms an angle of 45 degrees with a horizontal face X which goes through the centers O of the bearing support rings 71a and 73a, and the points A and C and the points B and D, respectively, fall on a diagonal line. Namely, the straight line connecting the points A and C comes to be vertical to the straight line connecting the points B and D, forming an angle of 45 degrees with the horizontal face X. The gap-measuring sensors 53 and 54 are mounted at the four points A through D of the bearing support rings 71a and 73a in this manner, so as to measure the change in gaps in four directions of the shafts 3a and 5a.

Wherein, the displacement magnitude of the center positions of the shafts 3a and 5a is obtained when the dimensions (gaps) to the side walls of the shafts 3a and 5a that are measured by the gap-measuring sensors 53 and 54 at the points A through D of the bearing support rings 71a and 73a, respectively, are supplied to the shaft-misalignment operating section 101. Namely, when the gaps GA1 through GD1 to the side wall of the shaft 3a are measured by the gap-measuring sensor 53 at the points A through D of the bearing support ring 71a, respectively, and when the gaps GA2 through GD2 to the side wall of the shaft 5a are measured by the gap-measuring sensor 54 at the points A through D of the bearing support ring 73a, respectively, the displacement magnitude $\Delta$d1 of the center position of the shaft 3a is obtained from the formula (3), and the displacement magnitude $\Delta$d2 of the center position of the shaft 5a is obtained from the formula (4). The displacement magnitudes $\Delta$d1 and $\Delta$d2 are the displacement magnitudes in the vertical direction to the horizontal face X.

$$\Delta d1 = ((GC1 - GA1) + (GB1 - GD1))/(2 \times 2^{1/2}) \tag{3}$$

$$\Delta d2 = ((GC2 - GA2) + (GB2 - GD2))/(2 \times 2^{1/2}) \tag{4}$$

By having the shaft-misalignment operating section 101 calculate as described in the above manner based on the measurements obtained by the gap-measuring sensor 53, it is confirmed, as shown in FIG. 3B, that the center of the shaft 3a at the bearing 71 drifts for an amount $\Delta$d1. Also, by having the shaft-misalignment operating section 101 calculate based on the measurements obtained by the gap-measuring sensor 54, it is confirmed, as shown in FIG. 3B, that the center of the shaft 5a at the bearing 73 drifts for an amount $\Delta$d2.

Further, the gap-measuring sensors 55u and 56u are mounted in the neighborhood of the point "u" of the flanges 3c and 5c so as to measure the dimensions (gaps) to the point "u" of the flanges 3c and 5c above the shafts 3a and 5a; and the gap-measuring sensors 55d and 56d are mounted in the neighborhood of the point "d" of the flanges 3c and 5c so as to measure the gaps to the point "d" of the flanges 3c and 5c below the shafts 3a and 5a. When the amount of change in gaps measured by the gap-measuring sensors 55u and 55d mounted at the points "u" and "d" of the flange 3c and the amount of change in gaps measured by the gap-measuring sensors 56u and 56d mounted at the points "u" and de of the flange 5c are supplied to the shaft-misalignment operating section 101, the misalignment amount of the shafts 3a and 5a due to inclination is obtained.

In other words, when the amount Gu1 of change in dimension (gap) to the point "u" in the upper part of the flange 3c is measured by the gap-measuring sensor 55u; the amount Gd1 of change in dimension (gap) to the point "d" in the lower part of the flange 3c is measured by the gap-measuring sensor 55d; the amount Gu2 of change in dimension (gap) to the point "u" in the upper part of the flange 5c is measured by the gap-measuring sensor 56u; and the amount Gd2 of change in dimension (gap) to the point "d" in the lower part of the flange 5c is measured by the gap-measuring sensor 56d respectively, the shaft-misalignment amount $\Delta$S1 due to inclination of the shaft 3a is obtained from the formula (5) and the shaft-misalignment amount $\Delta$S2 due to inclination of the shaft 5a is obtained from the formula (6). Here ds1 represents the dimension between the locations where the gap-measuring sensors 55$u$ and 55$d$ are mounted, and ds2 represents the dimension between the locations where the gap-measuring sensors 56$u$ and 56$d$ are mounted, respectively. The amounts Gu1, Gd1, Gu2 and Gd2 of change in gaps are zero (0), respectively, when the shafts 3$a$ and 5$a$ are installed without inclination.

$$\Delta S1 = (Gu1 - Gd1)/ds1 \quad (5)$$

$$\Delta S2 = (Gu2 - Gd2)/ds2 \quad (6)$$

Wherein, as shown in FIG. 3C, by having the shaft-misalignment operating section 101 calculate based on the measurements Gu1 and Gd1 obtained by the gap-measuring sensors 55$u$ and 55$d$, the shaft-misalignment amount $\Delta S1$ (=tan $\Delta \theta 1$) due to the inclination $\Delta \theta 1$ of the shaft 3$a$ is confirmed. Additionally, as shown in FIG. 3C, by having the shaft-misalignment operating seciton 101 calculate based on the measurements Gu2 and Gd2 obtained by the gap-measuring sensors 56$u$ and 56$d$, the shaft-misalignment amount $\Delta S2$ (=tan $\Delta \theta 2$) due to the inclination $\Delta \theta 2$ of the shaft 5$a$ is confirmed.

When the expansion amounts $\Delta hi1$ and $\Delta hi2$ of the bearing pedestals 72 and 74, the displacement magnitudes $\Delta d1$ and $\Delta d2$ of the center positions of the shafts 3$a$ and 5$a$ and the shaft-misalignment amounts $\Delta S1$ and $\Delta S2$ due to inclination of the shafts 3$a$ and 5$a$ are obtained, respectively, by the shaft-misalignment operating section 101 as described above, the shaft-misalignment amount "do" of the shafts 3$a$ and 5$a$ shown in FIG. 3C is obtained from the formula (7). Here, d0 represents the shaft-misalignment amount of the shafts 3$a$ and 5$a$ when installed; L1 represents the dimension between the engagement portion 70 of the clutch 7 and the center of the bearing pedestal 72; and L2 represents the dimension between the engagement portion 70 of the clutch 7 and the center of the bearing pedestal 74, respectively.

$$do = d0 + (\Delta hi1 + \Delta d1) + \Delta S1 \times L1 - (\Delta hi2 + \Delta d2) + \Delta S2 \times L2 \quad (7)$$

Figure 5:
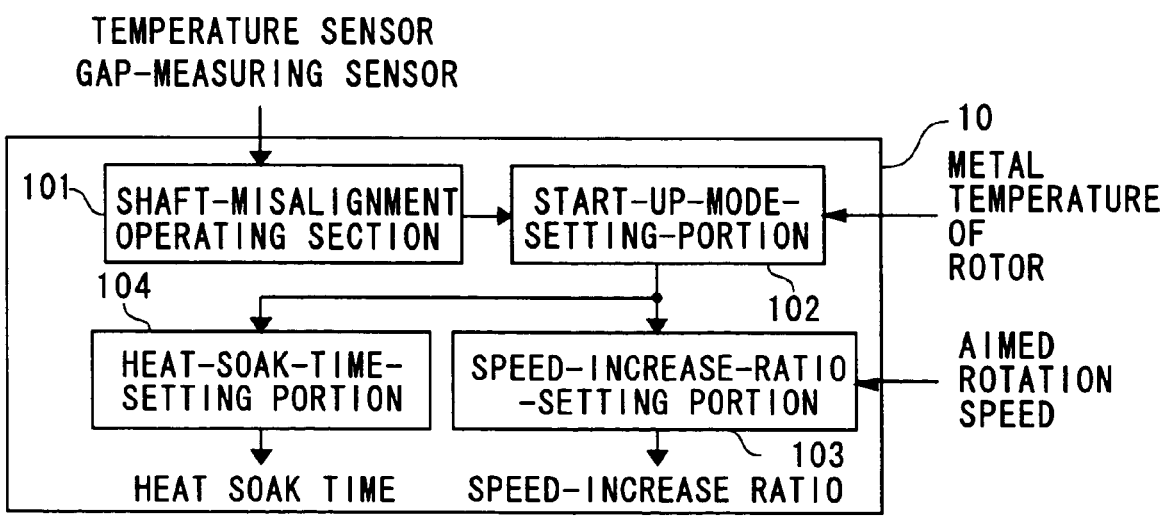
FIG. 5 is a block diagram showing an inner construction of a control equipment to be provided to a single-shaft combined plant in FIG. 1.

2. Construction of the Plant Start-Up Controlling Portion in the Control Equipment Next, a part of construction of the control equipment 10 of a single-shaft combined plant provided with a shaft-misalignment measuring device which measures the misalignment amount of the shafts 3$a$ and 5$a$ as mentioned above will be described hereafter. FIG. 5 is a block diagram showing a part of the construction of the control equipment 10.

As shown in FIG. 5, the control equipment 10 consists of a shaft-misalignment operating section 101 which calculates the shaft-misalignment amount "do" of the shafts 3$a$ and 5$a$; a start-up-mode-setting portion 102 which sets the action mode for the start-up time based on the shaft-misalignment amount "do" obtained by the shaft-misalignment operating section 101 and on the metal temperature of the rotor of the steam turbine 5; a speed-increase-ratio-setting portion 103 which sets the speed-increase ratio of the rotation speed of the steam turbine 5 in accordance with the action mode set by the start-up-mode-setting portion 102; and a heat-soak-time-setting portion 104 which sets the heat soak time, in accordance with the action mode set by the start-up-mode-setting portion 102, for rotating the steam turbine 5, by maintaining safe rotation speed.

Figure 6:
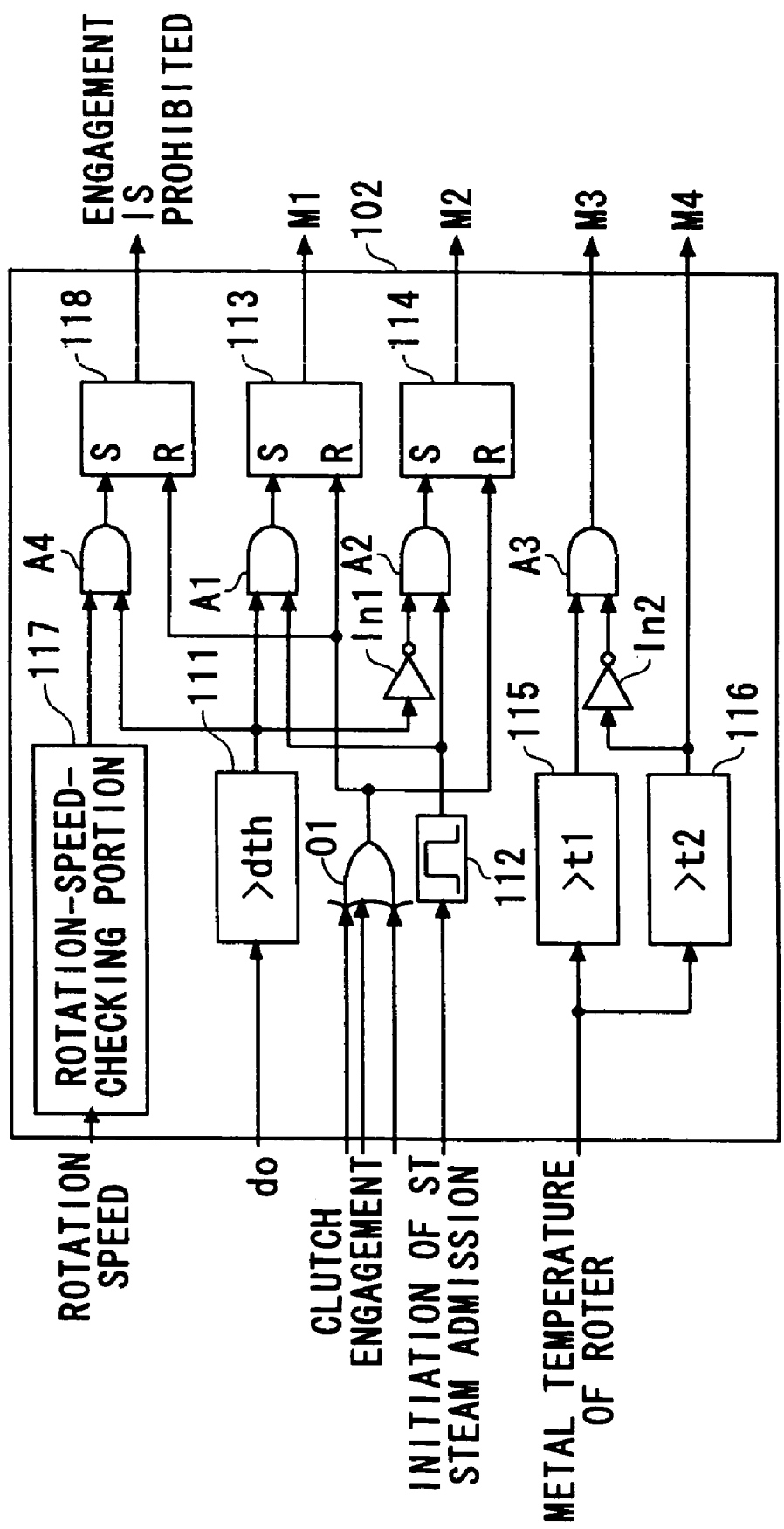
FIG. 6 is a block diagram showing an inner construction of a start-up-mode-setting portion of the control equipment in FIG. 5.

Moreover, as shown in FIG. 6, the start-up-mode-setting portion 102 consists of a comparator 111 which compares the shaft-misalignment amount "do" obtained by the shaft-misalignment operating section 101 with a threshold value dth; a pulse-generating circuit 112 which generates a pulse signal when steam starts to be supplied from the HRSG 4 to the steam turbine 5; an AND circuit A1 to which a signal from the comparator 111 and a pulse signal from the pulse-generating-circuit 112 are supplied; an inverter In1 which reverses a signal from the comparator 111; an AND circuit A2 to which a signal from the inverter In1 and a pulse signal from the pulse-generating-circuit 112 are supplied; an OR circuit O1 to which a signal is supplied to indicate whether the clutch 7 is engaged properly or not; an RS circuit 113 which outputs a "HIGH" signal by a signal from the AND circuit A1 and outputs a "LOW" signal by a signal from the OR circuit O1; an RS circuit 114 which outputs a "HIGH" signal by a signal from the AND circuit A2 and outputs a "LOW" signal by a signal from the OR circuit O1; comparators 115 and 116 which compare the supplied temperature information concerning the metal temperature of the rotor which is the metal temperature at the inlet of the first stage of the steam turbine 5, with threshold values t1 and t2 (t2>t1); an inverter In2 which reverses a signal from the comparator 116; an AND circuit A3 to which a signal from the comparator 115 and a signal from the inverter In2 are supplied; a rotation-speed-checking portion 117 which confirms that the steam turbine 5 attains a predetermined rotation speed which is near the rated rotation speed; an AND circuit A4 to which signals from the comparator 111 and the rotation-speed-checking portion 117, respectively, are supplied; and an RS circuit 118 which outputs a "HIGH" signal by a signal from the AND circuit A4 and outputs a "LOW" signal by a signal from the OR circuit 01.

When the start-up-mode-setting portion 102 is set as described above, and in case where the shaft-misalignment amount "do" is larger than the threshold value dth, a "HIGH" signal is output from the comparator 111. Then, because a pulse signal is generated by the pulse-generating circuit 112 when it is confirmed that the steam starts to be supplied from the HRSG 4 to the steam turbine 5 so as to actuate the steam turbine 5, a "HIGH" signal is supplied to the RS circuit 113 from the AND circuit A1 and a "LOW" signal is supplied to the RS circuit 114 from the AND circuit A2. Consequently, the signal from the RS circuit 113 is a "HIGH" signal, whereas the signal from the RS circuit 114 is a "LOW" signal. As a result, a signal M1 is output from the RS circuit 113, showing a large shaft-alignment-amount mode in which the shaft-alignment amount of the shafts 3$a$ and 5$a$ in the clutch 7 is large.

When the shaft-alignment amount "do" is equals to the threshold value "dth" or less, a "LOW" signal is output by the comparator 111. Then, because a pulse signal is generated in the pulse-generating-circuit 112 when it is confirmed that steam starts to be supplied from the HRSG 4 to the steam turbine 5 so as to actuate the steam turbine 5, a "LOW" signal is supplied to the RS circuit 113 from the AND circuit A1, whereas a "HIGH" signal is supplied to the RS circuit 114 from the AND circuit A2. Consequently, the signal from the RS circuit 113 is a "LOW" signal, whereas the signal from the RS circuit 114 is a "HIGH" signal. As a result, a signal M2 is output from the RS circuit 114, showing a small shaft-misalignment-amount mode in which the shaft-misalignment amount of the shafts 3$a$ and 5$a$ in the clutch 7 is small. When this signal M2 showing the small shaft-misalignment-amount mode is supplied, it is confirmed that engagement action of the clutch 7 can be executed in a stable manner in the control equipment 10, and ordinary start-up action is performed.

When the metal temperature of the rotor of the steam turbine 5 is equal to the threshold value t1 or less, "LOW" signals are output from the comparators 115 and 116, and as a result, "LOW" signals are output from the comparator 116 and the AND circuit A3, thereby showing the cold mode. When the metal temperature of the rotor of the steam turbine 5 is higher than the threshold value t1 but is equivalent to t2 or less, a "HIGH" signal is output from the comparator 115 and a "LOW" signal is output from the comparator 116; and as a result, a "LOW" signal is output from the comparator 116 and a "HIGH" signal is output from the AND circuit A3, thereby showing the warm mode. When the metal temperature of the rotor of the steam turbine 5 is higher than the threshold value t2, "HIGH" signals are output from the comparators 115 and 116; and as a result, a "HIGH" signal is output from the comparator 116 and a "LOW" signal is output from the AND circuit A3, thereby showing the hot mode.

Further, when it is confirmed that the rotation speed of the steam turbine 5 reaches a rotation speed which is lower than the rated rotation speed for a predetermined amount, a "HIGH" signal is output from the rotation-speed-checking portion 117. At this time, when the shaft-misalignment amount "do" is equal to the threshold value "dth" or less, a "LOW" signal is output from the comparator 111 and a "LOW" signal is supplied to the RS circuit 118 from the AND circuit A4, resulting in output of a "LOW" signal from the RS circuit 118. When the shaft-misalignment amount "do" is larger than the threshold value dth, a "HIGH" signal is output from the comparator 111 and a "HIGH" signal is supplied to the RS circuit 118 from the AND circuit A4, resulting in output of a "HIGH" signal from the RS circuit 118, thereby prohibiting the engagement action of the clutch 7. When a signal showing that the engagement action of the clutch 7 is properly performed is supplied to the OR circuit O1, "HIGH" signals are supplied to the RS circuits 113, 114 and 118 from the OR circuit O1, resulting in "LOW" signals from the RS circuits 113, 114 and 118.

Figure 7:
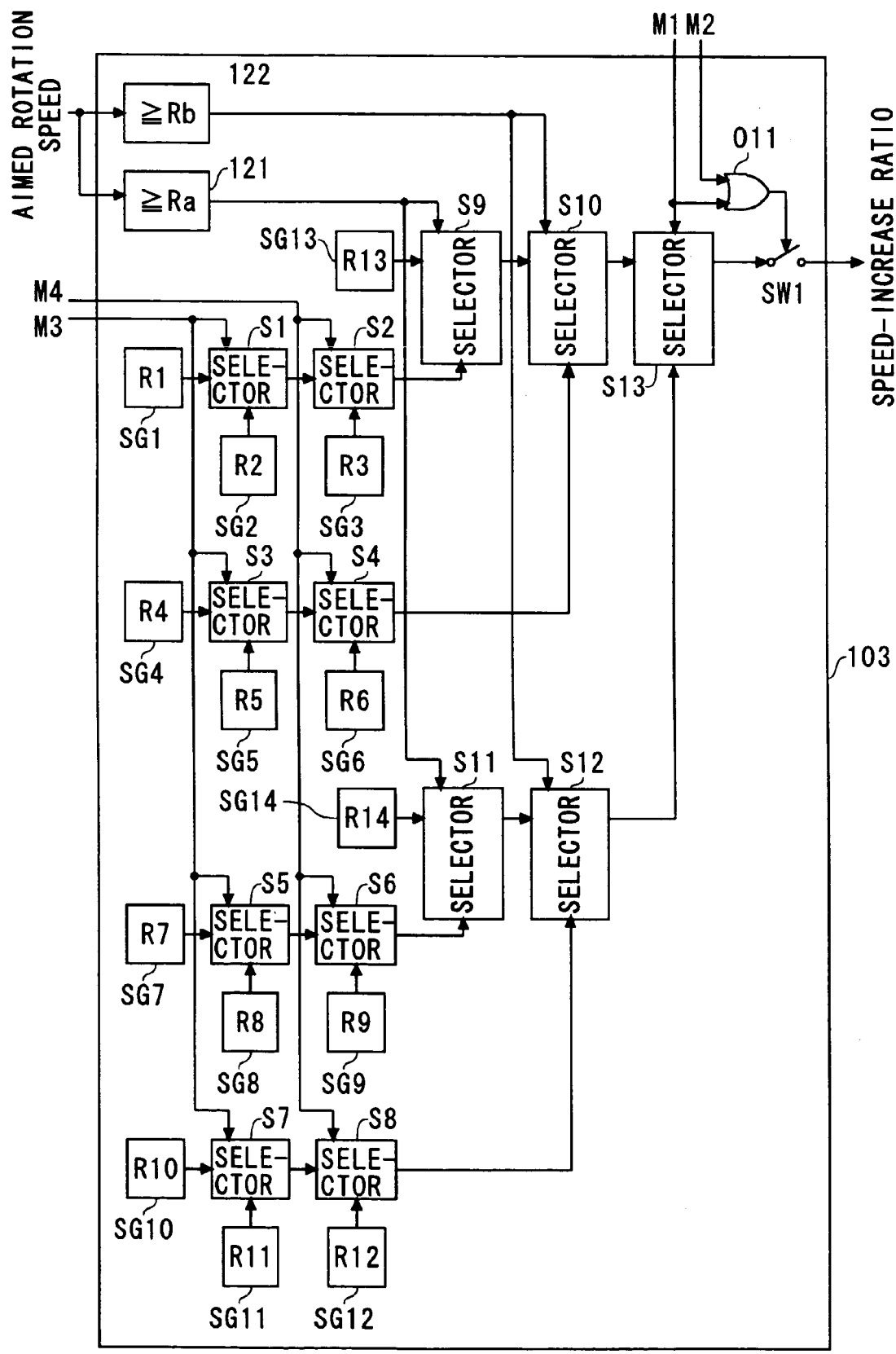
FIG. 7 is a block diagram showing an inner construction of a speed-increase-ratio-setting portion of the control equipment in FIG. 5.

As shown in FIG. 7, the speed-increase-ratio-setting portion 103 consists of signal-generators SG1 through SG14 which output signals of speed-increase ratios R1 through R14 [rpm/min.]; a selector S1 which selects one signal from the signals from the signal-generators SG1 and SG2 respectively; a selector S2 which selects one signal from the signals from the selector S1 and the signal-generator SG3, respectively; a selector S3 which selects one signal from the signals from the signal-generators SG4 and SG5, respectively; a selector S4 which selects one signal from the signals from the selector S3 and the signal-generator SG6, respectively; a selector S5 which selects one signal from the signals from the signal-generators SG7 and SG8, respectively; a selector S6 which selects one signal from the signals from the selector S5 and the signal-generator SG9, respectively; a selector S7 which selects one signal from the signals from the signal-generators SG10 and SG11, respectively; a selector S8 which selects one signal from the signals from the selector S7 and the signal-generator SG12, respectively; a selector S9 which selects one signal from the signals from the selector S2 and the signal-generator SG13, respectively; a selector S10 which selects one signal from the signals from the selectors S4 and S9, respectively; a selector S11 which selects one signal from the signals from the selector S6 and the signal-generator SG14, respectively; a selector S12 which selects one signal from the signals from the selectors S8 and S11, respectively; a selector S13 which selects one signal from the signals from the selectors S10 and S12, respectively; an OR circuit O11 to which signals M1 and M2 are supplied; a switch SW1 which is controlled by the output from the OR circuit O11; a comparator 121 which outputs a signal M5 when the aimed rotation speed of the steam turbine 5 is more than Ra; and a comparator 122 which outputs a signal M6 when the aimed rotation speed of the steam turbine 5 is more than Rb.

Wherein, when signals M3 from the AND circuit A3 are supplied to the selectors S1, S3, S5 and S7 and when the signals M3 are "LOW" signals, the selector S1 selects a signal from the signal-generator SG1, the selector S3 selects a signal from the signal-generator SG4, the selector S5 selects a signal from the signal-generator SG7 and the selector S7 selects a signal from the signal-generator SG10, respectively. When the signals M3 are "HIGH" signals, the selector S1 selects a signal from the signal-generator SG2, the selector S3 selects a signal form the signal-generator SG5, the selector S5 selects a signal from the signal-generator SG8, and the selector S7 selects a signal from the signal-generator SG11, respectively. Moreover, when signals M4 from the comparator 116 are supplied to the selectors S2, S4, S6 and S8 and when the signals M4 are "LOW" signals, the selector S2 selects a signal from the selector S1, the selector S4 selects a signal from the selector S3, the selector S6 selects a signal from the selector S5, and the selector S8 selects a signal from the selector S7, respectively. When the signals M4 are "HIGH" signals, the selector S2 selects a signal from the signal-generator SG3, the selector S4 selects a signal from the signal-generator SG6, the selector S6 selects a signal from the signal-generator SG9 and the selector S8 selects a signal form the signal-generator SG12, respectively.

Further, when signals M5 indicating that the aimed rotation speed of the steam turbine 5 is more than Ra are supplied to the selectors S9 and S11 from the comparator 121 and when the signals M5 are "LOW" signals, the selector S9 selects a signal from the signal-generator SG13 and the selector S11 selects a signal from the signal-generator SG14, respectively. When the signals M5 are "HIGH" signals, the selector S9 selects a signal from the selector S2 and the selector S11 selects a signal from the selector S6, respectively. Moreover, when signals M6 indicating that the aimed rotation speed of the steam turbine is more than Rb are supplied to the selectors S10 and S12 from the comparator 122 and when the signals M6 are "LOW" signals, the selector S10 selects a signal from the selector S9 and the selector S12 selects a signal from the selector S11, respectively. Also, when the signals M6 are "HIGH" signals, the selector S10 selects a signal from the selector S4 and the selector S12 selects a signal from the selector S8, respectively. When a signal M1 from the RS circuit 113 is supplied to the selector S13 and when the signal M1 is a "LOW" signal, the selector S13 selects a signal from the selector S10; and when the signal M1 is a "HIGH" signal, the selector S13 selects a signal from the selector S12.

Further, because the signals M1 and M2 are supplied to the OR circuit O11 from the RS circuits 113 and 114, when either of the signals M1 and M2 is a "HIGH" signal, the signal from the OR circuit O11 is a "HIGH" signal and the switch SW1 is placed ON. Then, the signal selected by the selector S13 is output as a signal which sets the speed-increase ratio of the steam turbine 5. However, when both of the signals M1 and M2 are "LOW" signals, the signal from the OR circuit O11 is a "LOW" signal and the switch SW1 is placed OFF, thereby prohibiting output of the signal selected by the selector S13. When the speed-increase-ratio-setting portion 103 is constructed in this manner, action in each mode is as follows.

(1) Small Shaft-Alignment Mode
a. When the Aimed Rotation Speed is Lower than Ra:

Because the signal M2 is a "HIGH" signal and the signals M1 and M3 through M6 are "LOW" signals, the speed-increase ratio R13 of the signal-generator SG13 is selected by the selectors S9, S10 and S13 and output by way of the switch SW1.

b. When the Aimed Rotation Speed is More than Ra but Lower than Rb:

b-1. Cold Mode

Because the signals M2 and M5 are "HIGH" signals but the signals M1, M3, M4 and M6 are "LOW" signals, the speed-increase ratio R1 of the signal-generator SG1 is selected by the selectors S1, S2, S9, S10 and S13 and output by way of the switch SW1.

b-2. Warm Mode

Because the signals M2, M3 and M5 are "HIGH" signals but the signals M1, M4 and M6 are "LOW" signals, the speed-increase ratio R2 of the signal-generator SG2 is selected by the selectors S1, S2, S9, S10 and S13 and output by way of the switch SW1.

b-3. Hot Mode

Because the signals M2, M4 and M5 are "HIGH" signals but the signals M1, M3 and M6 are "LOW" signals, the speed-increase ratio R3 of the signal-generator SG3 is selected by the selectors S2, S9, S10 and S13 and output by way of the switch SW1.

c. When the Aimed Rotation Speed is More than Rb:

c-1. Cold Mode

Because the signals M2, M5 and M6 are "HIGH" signals but the signals M1, M3 and M4 are "LOW" signals, the speed-increase ratio R4 of the signal-generator SG4 is selected by the selectors S3, S4, S10 and S13 and output by way of the switch SW1.

c-2. Warm Mode

Because the signals M2, M3, M5 and M6 are "HIGH" signals but the signals M1 and M4 are "LOW" signals, the speed-increase ratio R5 of the signal-generator SG5 is selected by the selectors S3, S4, S10 and S13 and output by way of the switch SW1.

c3. Hot Mode

Because the signals M2 and M4 through M6 are "HIGH" signals but the signals M1 and M3 are "LOW" signals, the speed-increase ratio R6 of the signal-generator SG6 is selected by the selectors S4, S10 and S13 and output by way of the switch SW1.

Large Shaft-Misalignment Mode a. When the Aimed Rotation Speed is Lower than Ra:

Because the signal M1 is "HIGH" signals but the signals M2 through M6 are "LOW" signals, the speed-increase ratio R14 of the signal-generator SG14 is selected by the selectors S11 through S13 and output by way of the switch SW1.

b. When the Aimed Rotation Speed is More than Ra but Lower than Rb, b-1. Cold Mode Because the signals M1 and M5 are "HIGH" signals but the signals M2 through M4 and M6 are "LOW" signals, the speed-increase ratio R7 of the signal-generator SG7 is selected by the selectors S5, S6 and S11 through S13 and output by way of the switch SW1.

b-2. Warm Mode

Because the signals M1, M3 and M5 are "HIGH" signals but the signals M2, M4 and M6 are "LOW" signals, the speed-increase ratio R8 of the signal-generator SG8 is selected by the selectors S5, S6 and S11 through S13 and output by way of the switch SW1.

b-3. Hot Mode

Because the signals M1, M4 and M5 are "HIGH" signals but the signals M2, M3 and M6 are "LOW" signals, the speed-increase ratio R9 of the signal-generator SG9 is selected by the selectors S6 and S11 through S13 and are output by way of the switch SW1.

c. When the Aimed Rotation Speed is More than Rb:

c-1. Cold Mode

Because the signals M1, M5 and M6 are "HIGH" signals but the signals M2, M3 and M4 are "LOW" signals, the speed-increase ratio R10 of the signal-generator SG10 is selected by the selectors S7, S8, S12 and S13 and output by way of the switch SW1.

c-2. Warm Mode

Because the signals M1, M3, M5 and M6 are "HIGH" signals but the signals M2 and M4 are "LOW" signals, the speed-increase ratio R11 of the signal-generator SG11 is selected by the selectors S7, S8, S12 and S13 and output by way of the switch SW1.

c-3. Hot Mode

Because the signals M1 and M4 through M6 are "HIGH" signals but the signals M2 and M3 are "LOW" signals, the speed-increase ratio R12 of the signal generator SG12 is selected by the selectors S8, S12 and S13 and output by way of the switch SW1.

Wherein, by making the relation of the speed-increase ratios R1 through R3 be $R1 \leq R2 \leq R3$, the relation of the speed-increase ratios R4 through R6 be $R4 \leq R5 \leq R6$, the relation of the speed-increase ratios R7 through R9 be and $R7 \leq R8 \leq R9$ and the relation of the speed-increase ratios R10 through R12 be $R10 \leq R11 \leq R12$, in the cold mode in which the metal temperature of the rotor of the steam turbine 5 is low, the speed-increase ratio is made small; whereas in the hot mode in which the metal temperature of the rotor of the steam turbine 5 is high, the speed-increase ratio is made large. By this, when the steam turbine 5 attains the rated rotation speed so as to have the clutch 7 engaged, it is possible to make the metal temperature of the rotor of the steam turbine 5 sufficiently high.

By making the relation of the speed-increase ratios R1 and R7 be $R1 \geq R7$ and the relation of the speed-increase ratios R4 and R10 be $R4 \geq R10$, in the small shaft-misalignment mode in which the misalignment of the shafts 3a and 5a is within the predetermined range, the speed-increase ratio is made large; whereas in the large shaft-misalignment mode in which the misalignment of the shafts 3a and 5a is larger than the predetermined range, the speed-increase ratio is made small. By this, when the shaft-misalignment is large at the start-up time of the steam turbine 5, by gradually increasing the rotation speed of the steam turbine 5 so as to raise the temperature of the drain oil from the bearing 73 high, thereby flowing the high temperature drain oil to the bearing pedestal 74, it is possible to change the expansion amount of the bearing pedestal 74 so as to reduce the misalignment of the shafts 3a and 5a. Also, when the shaft-misalignment at the start-up time of the steam turbine 5 is small, by rapidly increasing the rotation speed of the steam turbine 5 so as to have the clutch 7 engaged at an early stage, it is possible to receive the electrical output from the generator 6 soon.

Figure 8:
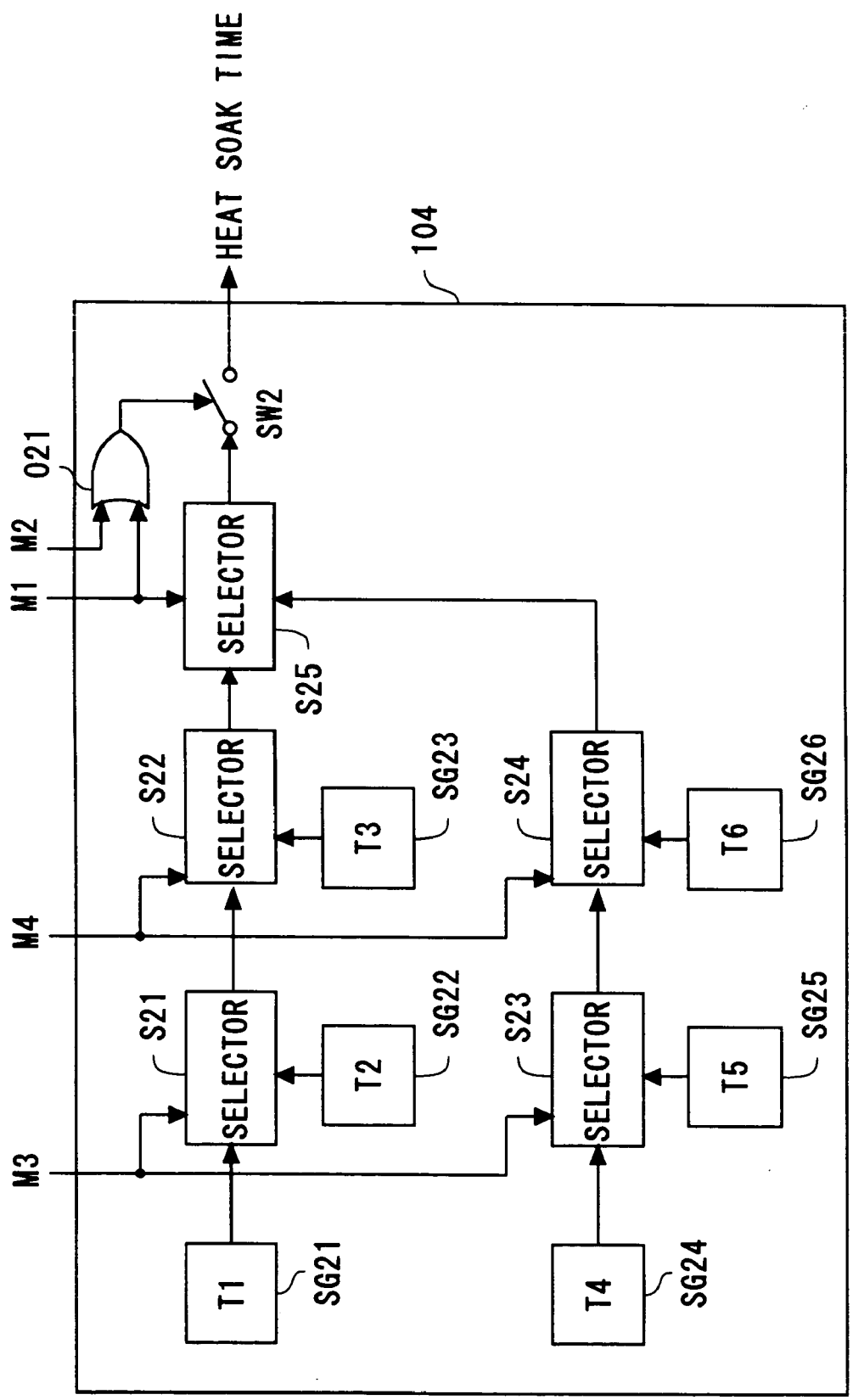
FIG. 8 is a block diagram showing an inner construction of a heat-soak-time-setting portion of the control equipment in FIG. 5.

The heat-soak-time-setting portion 104, as shown in FIG. 8, consists of signal-generators SG21 through SG26 which output signals of heat soak time T1 through T6 respectively; a selector 21 which selects one signal from the signals from the signal-generators SG21 and SG22, respectively; a selector S22 which selects one signal from the signals from the selector S21 and the signal-generator SG23, respectively; a selector S23 which selects one signal from the signals from the signal-generators SG24 and SG25, respectively; and a selector S24 which selects one signal from the signals from the selector S23 and the signal-generator SG26, respectively; a selector S25 which selects one signal from the signals from the selectors S22 and S24, respectively; an OR circuit O21 to which signals M1 and M2 are supplied; and a switch SW2 which is controlled by the output from the OR circuit O21.

Wherein, when signals M3 from the AND circuit A3 are supplied to the selectors S21 and S23 and when the signals M3 are "LOW" signals, the selector S21 selects the signal from the signal-generator SG21 and the selector S23 selects the signal from the signal-generator SG24, respectively. When the signals M3 are "HIGH" signals, the selector S21 selects the signal from the signal-generator SG22 and the selector S23 selects the signal form the signal-generator SG25, respectively. Moreover, when signals M4 from the comparator 116 are supplied to the selectors S22 and S24 and the signals M4 are "LOW" signals, the selector S22 selects the signal from the selector S21 and the selector S24 selects the signal from the selector S23, respectively. When the signals M4 are "HIGH" signals, the selector S22 selects the signal from the signal-generator SG23 and the selector S24 selects the signal from the signal-generator SG26, respectively.

When signals M1 from the RS circuit 113 are supplied to the selector S25 and when the signals M1 are "LOW" signals, the selector S25 selects the signal from the selector S22. When the signals M1 are "HIGH" signals, the selector S25 selects the signal from the selector S24. Further, because the signals M1 and M2 are supplied to the OR circuit O21 from the RS circuits 113 and 114, when either of the signals M1 and M2 is a "HIGH" signal, the signal from the OR circuit O21 is a "HIGH" signal and the switch SW2 is placed ON; thereby supplying the signal selected by the selector S25 as a signal which sets the speed-increase ratio of the steam turbine 5. However, when both of the signals M1 and M2 are "LOW" signals, the signal from the OR circuit O21 is a "LOW" signal and the switch SW2 is placed OFF, thereby prohibiting the output of the signal selected by the selector 25.

(1) Small Shaft-Alignment Mode a. Cold Mode

Because the signal M2 is a "HIGH" signal but the signals M1, M3 and M4 are "LOW" signals, the heat soak time T1 of the signal-generator SG21 is selected by the selectors S21, S22 and S25 and output by way of the switch SW2.

b. Warm Mode

Because the signals M2 and M3 are "HIGH" signals but the signals M1 and M4 are "LOW" signals, the heat soak time T2 of the signal-generator SG22 is selected by the selectors S21, S22 and S25 and output by way of the switch SW2.

c. Hot Mode

Because the signals M2 and M4 are "HIGH" signals but the signals M1 and M3 are "LOW" signals, the heat soak time T3 of the signal-generator SG23 is selected by the selectors S22 and S25 and output by way of the switch SW2.

(2) Large Shaft-Misalignment Mode a. Cold Mode

Because the signal M1 is a "HIGH" signal, but the signals M2 through M4 are "LOW" signals, the heat soak time T4 of the signal-generator SG24 is selected by the selectors S23, S24 and S25 and output by way of the switch SW2.

b. Warm Mode

Because the signals M1 and M3 are "HIGH" signals but the signals M2 and M4 are "LOW" signals, the heat soak time T5 of the signal-generator SG25 is selected by the selectors S23, S24 and S25 and output by way of the switch SW2.

c. Hot Mode

Because the signals M1 and M4 are "HIGH" signals but the signals M2 and M3 are "LOW" signals, the heat soak time T6 of the signal-generator SG26 is selected by the selectors S24 and S25 and output by way of the switch SW2.

Wherein, by making the relation of the heat soak time T1 through T3 be $T1 \geq T2 \geq T3$ and the relation of the heat soak time T4 through T6 be $T4 \geq T5 \geq T6$, in the cold mode in which the metal temperature of the rotor of the steam turbine 5 is low, the heat soak time is made large; whereas in the hot mode in which the metal temperature of the rotor of the steam turbine 5 is high, the heat soak time is made small. As described above, by making the heat soak time longer when the metal temperature of the rotor of the steam turbine 5 is low and by making the heat soak time shorter when the metal temperature of the rotor of the steam turbine 5 is high, it is possible to make the metal temperature of the rotor of the steam turbine 5 sufficiently high when the heat soak time is over.

Additionally, by making the relation of the heat soak time T1 and T4 be $T1 \leq T4$, in the small shaft-misalignment mode in which the misalignment of the shafts 3a and 5a is within the predetermined range, the heat soak time is made shorter, whereas in the large shaft-misalignment mode in which the misalignment of the shafts 3a and 5a is larger than the predetermined range, the heat soak time is made longer. By this, when the shaft-misalignment is large at the start-up time of the steam turbine 5, by prolonging the heat soak time so as to make the period until the steam turbine 5 attains the rated rotation speed longer and by making the temperature of the drain oil from the bearing 73 high, thereby flowing the high temperature drain oil flow to the bearing pedestal 74, it is possible to vary the expansion amount of the bearing pedestal 74, so as to make the misalignment of the shafts 3a and 5a small. When the shaft-misalignment at the start-up time of the steam turbine 5 is small, by shortening the heat soak time so as to make the period until the steam turbine 5 attains the rated rotation speed shorter, thereby having the clutch 7 engaged at an early stage, it is possible to receive the electrical output from the generator 6 soon.

3. Start-Up Action of the Plant

Figure 9:
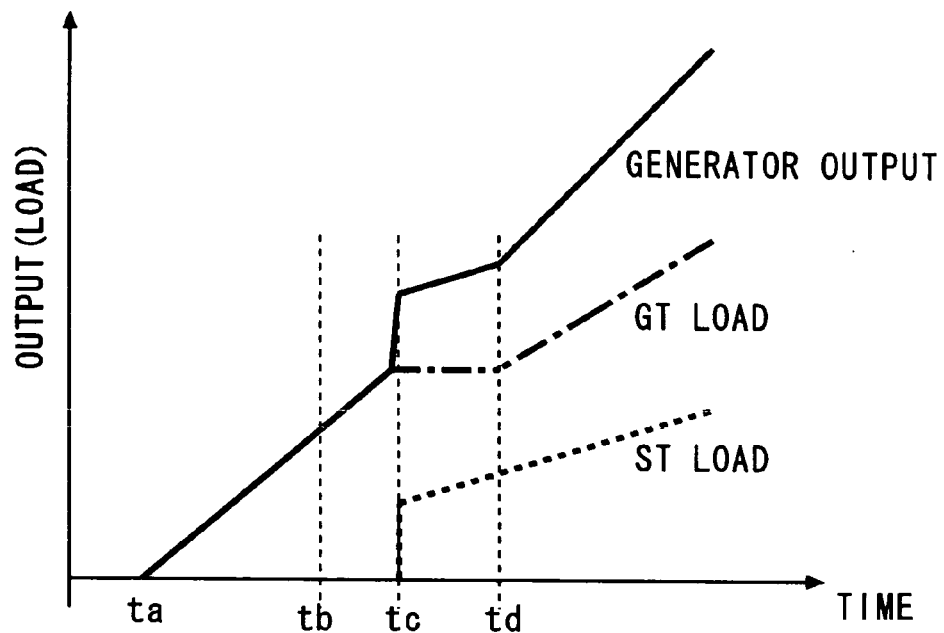
FIG. 9 is a timing chart which shows a change of load of an entire plant, a gas turbine and a steam turbine, respectively, at the start-up time of a single-shaft combined plant.

Next, actions at the start-up time of a single-shaft combined plant shown in FIG. 1 will be described hereafter. FIG. 9 is a timing chart which shows a change of load of an entire plant, a gas turbine 3 and a steam turbine 5, respectively, at the start-up time of a single-shaft combined plant. In FIG. 9, a solid line depicts the load of an entire plant, an alternate long and short dash line depicts the load of a gas turbine 3 and a dotted line depicts the load of a steam turbine 5, respectively.

First, the generator 6 is operated as a thyristor to rotate a gas turbine 3. At the time ta, the fuel and the air compressed by the compressor 1 are supplied to the combustor 2, where combustion gas is generated, and this combustion gas is supplied to the gas turbine 3. When the gas turbine 3 is rotated with the combustion gas in this manner, the generator 6 acts as an electric power generator, and the load thereof (the load of the entire plant) becomes equivalent to the load of the gas turbine 3. After that, by adjusting the flow rate of the fuel to the combustor 2 with a fuel-control valve 2b and by adjusting the flow rate of the air to the compressor 1 with the IGV 1a, the loads of the gas turbine 3 and the generator 6 are increased.

Then, at the time tb, when sufficient steam for operation of the steam turbine 5 is generated, the steam is supplied from the HRSG 4 to the steam turbine 5 to start operation thereof. Wherein, because the shafts 3a and 5a are disconnected by the clutch 7, rotation of the steam turbine 5 is not transmitted to the generator 6. Consequently, there is no load of the steam turbine 5. When the steam turbine 5 starts rotation in this manner, the control equipment 10 confirms the metal temperature of the rotor of the steam turbine 5, the shaft-misalignment amount of the shafts 3a and 5a and the aimed rotation speed of the steam turbine 5 as described above. Subsequently, the speed-increase ratio and the heat soak time are set in accordance with the metal temperature of the rotor of the steam turbine 5, the shaft-misalignment amount of the shafts 3a and 5a and the aimed rotation speed of the steam turbine 5 that are confirmed.

Figure 10:
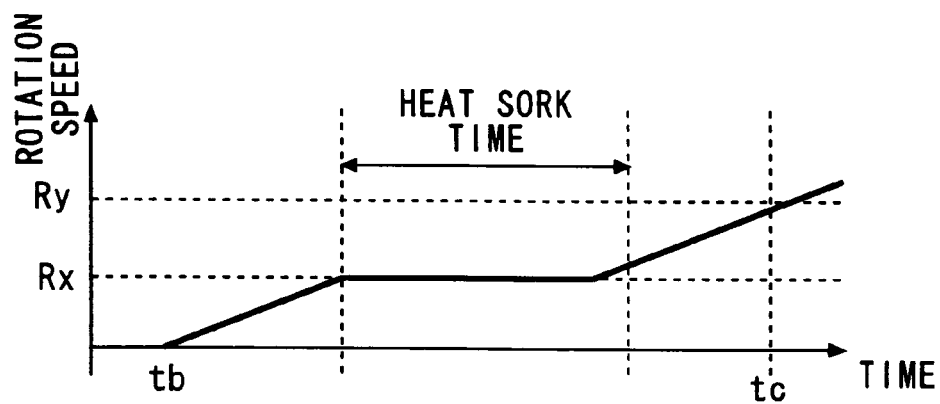
FIG. 10 is a timing chart which shows a change of rotation speed of a steam turbine.
Figure 11:
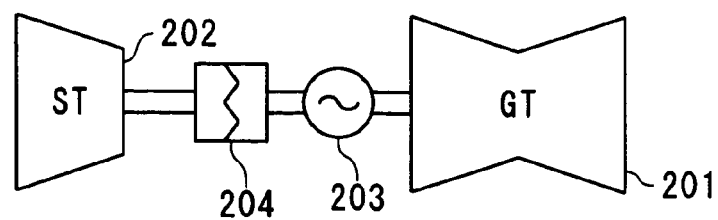
FIG. 11 is a block diagram showing the construction of a conventional single-shaft combined plant.

When the speed-increase-ratio and the heat soak time of the steam turbine 5 are set as described above, as shown in FIG. 10, first, by adjusting the flow rate of steam being supplied to the steam turbine 5 with the governing valve 5b, the rotation speed is increased at the set speed-increase ratio until the predetermined rotation speed Rx for heat soak. Then, when the rotation speed of the steam turbine 5 attains the predetermined rotation speed Rx, the steam turbine 5 is rotated at this predetermined rotation speed Rx for a period of the set heat soak time. Subsequently, the rotation speed of the steam turbine 5 is increased again at the set speed-increase ratio. Then, when the rotation speed of the steam turbine 5 approaches the rotation speed Ry of the gas turbine 3 (the rated rotation speed mentioned above), the shafts 3a and 5a are connected by engagement of the clutch 7. At this time, when the misalignment amount of the shafts 3a and 5a is determined to be large by the control equipment 10, engagement action of the clutch 7 is prohibited.

In acting as described above, as shown in FIG. 9, at the time tc, the rotation speed of the steam turbine 5 approaches the rotation speed of the gas turbine 3 and the shafts 3a and 5a are connected by the clutch 7, so that the rotation of the steam turbine 5 is transmitted to the generator 6 by the shafts 3a and 5a. Around the time tc when the steam turbine 5 is connected to the gas turbine 3, the gas turbine 3 has the rotation speed thereof fixed, so that a fixed load will be output. Consequently, the load of the generator 6 becomes large in accordance with the load of the steam turbine 5 until the time td. Then, when the time td comes, the opening of the IGV 1a, the fuel-control valve 2b and the governing valve 5b are adjusted so as to increase both loads of the gas turbine 3 and the steam turbine 5. In this way, the load of the generator 6 is increased at the set variation rate so that the load of the generator 6 will be as much as the aimed load.

In the embodiment according to the present invention, two action modes, i.e. the small shaft-misalignment mode and the large shaft-misalignment mode, are set for the shaft-misalignment amount of the shafts 3a and 5a by the start-up-mode-setting portion 102 of the control equipment 10. However, more than three action modes may be set, by having more than two threshold values. Additionally, in the embodiment according to the present invention, the control equipment 10 consists of blocks shown in FIG. 5 through FIG. 8. However, the invention is not limited to this construction, but such a software may be provided; wherein, the speed-increase ratio is reduced but the heat soak time is increased when the shaft-misalignment amount becomes larger; whereas the speed-increase ratio is increased but the heat soak time is reduced when the shaft-misalignment amount becomes smaller. Further, as shown in the disclosed embodiment, the control equipment 10 may be provided with a software which sets the speed-increase ratio and the heat soak time based on each of the actions depending on the shaft-misalignment amount of the shafts 3a and 5a and based on the metal temperature of the rotor of the steam turbine 5.

In accordance with the present invention, it is possible to measure the misalignment amount of a first shaft and a second shaft from the expansion amounts of bearing pedestals. Therefore, when the first shaft and the second shaft are connected by a clutch connecting the first shaft and the second shaft, and the like, it is possible to check whether the shaft-misalignment amount is within a permissible range or not. Additionally, because the misalignment amount of the first shaft and the second shaft can be measured from the information obtained by the gap-measuring sensors without contact, in measuring the shaft-misalignment amount of a body of revolution, it is possible to measure the shaft-misalignment thereof without disturbing rotation thereof. Because the shaft-misalignment amount can be measured as described above; when the first shaft and the second shaft are connected by the clutch, it is possible to stop connecting, thereby preventing a damage of the clutch, in case where the shaft-misalignment amount is out of the permissible range. Further, because, in a single-shaft combined plant, the operation method of a steam turbine can be changed in accordance with the shaft-misalignment amount, it is possible to make the temperature of the drain oil flowing through the bearing pedestals of a steam turbine sufficiently high so as to obtain the expansion amount thereof which is equivalent to the expansion amount of the bearing pedestals of a gas turbine. Consequently, when the shaft of the gas turbine and the shaft of the steam turbine are connected by a clutch, the shaft-misalignment amount can be restrained to be within the permissible range, thereby preventing the clutch from being damaged.

What is claimed is:

1. A shaft-misalignment-measuring device comprising:
    a plurality of first gap-measuring sensors that are mounted at a plurality of points in a circumferential direction of a first bearing where a first shaft of a first body of revolution is mounted;
    a plurality of second gap-measuring sensors that are mounted at a plurality of points in a circumferential direction of a second bearing where a second shaft of a second body of revolution is mounted; and
    a shaft-misalignment operating section which obtains misalignment of center of said first shaft from center of said first bearing from dimensions between a plurality of said points in a circumferential direction of said first bearing and said first shaft that are measured by said first gap-measuring sensors; obtains misalignment of center of said second shaft from center of said second bearing from dimensions between a plurality of said points in a circumferential direction of said second bearing and said second shaft that are measured by said second gap-measuring sensors; and calculates a part of shaft-misalignment amount of said first and second shafts based on misalignment of centers of said first and second shafts.

2. A shaft-misalignment-measuring device as described in claim 1 further comprising:
    a first temperature sensor which measures temperature of a first bearing pedestal supporting said first bearing; and
    a second temperature sensor which measures temperature of a second bearing pedestal supporting said second bearing;

wherein, said shaft-misalignment operating section obtains expansion amount of said first bearing pedestal from temperatures that are measured by said first temperature sensor; obtains expansion amount of said second bearing pedestal from temperatures that are measured by said second temperature sensor; and obtains a part of shaft-misalignment amount of said first and second shafts based on expansion amounts of said first and second bearing pedestals.

3. A shaft-misalignment-measuring device as described in claim 2;
wherein, a difference in expansion amount between said first and second bearing pedestals is a part of shaft-misalignment amount of said first and second shafts.

4. A shaft-misalignment-measuring device as described in claim 1;
wherein, said first gap-measuring sensor is placed so as to be in axial symmetry to a straight line being vertical to a horizontal surface of a cross section which is vertical to axial direction of said first bearing as well as in point symmetry to center of said first bearing; and
wherein said second gap-measuring sensor is placed so as to be in axial symmetry to a straight line being vertical to a horizontal surface of a cross section which is vertical to axial direction of said second bearing as well as in point symmetry to center of said second bearing.

5. A shaft-misalignment-measuring device as described in claim 4;
wherein, after obtaining a difference between dimensions to said first shaft that are measured by every two of said first gap-measuring sensors being in point symmetry to each other, an average of relevant differences in dimensions to said first shaft that are measured by every two of said first gap-measuring sensors being in point symmetry to each other is made to be misalignment of center of said first shaft from center of said first bearing;
wherein, after obtaining a difference between dimensions to said second shaft that are measured by every two of said second gap-measuring sensors being in point symmetry to each other, an average of relevant differences in dimensions to said second shaft that are measured by every two of said second gap-measuring sensors being in point symmetry to each other is made to be misalignment of center of said second shaft from center of said second bearing; and
wherein, a difference between misalignment of each center of relevant first and second shafts is a part of shaft-misalignment amount of said first and second shafts.

6. A shaft-misalignment-measuring device as described in claim 5 further comprising:
a third gap-measuring sensor which measures dimension to a first fixed point on an upper side of said first shaft;
a fourth gap-measuring sensor which measures dimension to a second fixed point on a lower side of said first shaft on a same surface with said first fixed point;
a fifth gap-measuring sensor which measures dimension to a third fixed point on an upper side of said second shaft; and
a sixth gap-measuring sensor which measures dimension to a fourth fixed point on a lower side of said second shaft on a same surface with said third fixed point; and
wherein, said shaft-misalignment operating section obtains inclination of said first shaft from dimensions to said first and second fixed points that are measured by said third and fourth gap-measuring sensors; obtains inclination of said second shaft from dimensions to said third and fourth fixed points that are measured by said fifth and sixth gap-measuring sensors; and obtains a part of shaft-misalignment amount of said first and second shafts based on inclination of said first and second shafts.

7. A shaft-misalignment-measuring device as described in claim 6;
wherein, where dimension between said third and fourth gap-measuring sensors is d1;
where dimensions to said first and second fixed points measured by said third and fourth gap-measuring sensors are du1 and dd1, respectively;
where dimension between a supporting point where said first shaft is supported and a connecting point where said first and second shafts are connected is D1;
where dimension between said fifth and sixth gap-measuring sensors is d2;
where dimensions to said third and fourth fixed points measured by said fifth and sixth gap-measuring sensors are du2 and dd2, respectively, and
where dimension between a supporting point where said second shaft is supported and a connecting point where said first and second shafts are connected is D2,
value of D1×(du1−dd1)/d1+D2×(du2−dd2)/d2 is a part of shaft-misalignment amount of said first and second shafts.

8. A single-shaft combined plant, comprising:
a shaft-misalignment-measuring device in accordance with claim 1;
a gas turbine which serves as said first body of revolution;
a steam turbine which serves as said second body of revolution;
a clutch which connects and disconnects said first shaft and said second shaft; and
wherein, action of said clutch to connect said first and second shafts is controlled in accordance with shaft-misalignment amount of said first and second shafts that is measured by said shaft-misalignment-measuring device.

9. A shaft-misalignment-measuring method comprising following steps:
a first step, wherein expansion amount of a first bearing pedestal supporting a first bearing where a first shaft of a first body of revolution is mounted and expansion amount of a second bearing pedestal supporting a second bearing where a second shaft of a second body of revolution is mounted are obtained;
a second step, wherein misalignment of center of said first shaft from center of said first bearing and misalignment of center of said second shaft from center of said second bearing are obtained;
a third step, wherein inclination of said first shaft and inclination of said second shaft are obtained; and
a fourth step, wherein shaft-misalignment amount of said first and second shafts is obtained based on a difference between expansion amounts of said first and second bearing pedestals, a difference between misalignment of center of said first shaft from center of said first bearing and misalignment of center of said second shaft from center of said second bearing, and inclination of said first and second shafts.

10. A shaft-misalignment measuring method described in claim 9;

wherein, in said first step, expansion amounts of said first and second bearing pedestals are obtained respectively from each of temperatures of said first and second bearing pedestals.

11. A shaft-misalignment measuring method as described in claim 9;
wherein, in said second step, misalignment of center of said first shaft from center of said first bearing is obtained from dimensions to said first shaft from a plurality of points in a circumferential direction of said first bearing; and
wherein, misalignment of center of said second shaft from center of said second bearing is obtained from dimensions to said second shaft from a plurality of points in a circumferential direction of said second bearing.

12. A shaft-misalignment-measuring device as described in claim 11;
wherein, a plurality of said points in a circumferential direction of said first bearing are placed so as to be in axial symmetry to a straight line being vertical to a horizontal surface of a cross section which is vertical to axial direction of said first bearing as well as in point symmetry to center of said first bearing;
wherein, a plurality of said points in a circumferential direction of said second bearing are placed so as to be in axial symmetry to a straight line being vertical to a horizontal surface of a cross section which is vertical to axial direction of said second bearing as well as in point symmetry to center of said second bearing;
wherein, in said second step, after obtaining differences between dimensions to said first shaft that are measured at every two of a plurality of said points in a circumferential direction of said first bearing being in point symmetry to each other, an average of the relevant differences in dimensions to said first shaft that are measured at every two of a plurality of said points in a circumferential direction of said first bearing being in point symmetry to each other is made to be misalignment of center of said first shaft from center of said first bearing; and
wherein, after obtaining differences between dimensions to said second shaft that are measured at every two of a plurality of said points in a circumferential direction of said second bearing being in point symmetry to each other, an average of relevant differences in dimensions to said second shaft that are measured at every two of a plurality of said points in a circumferential direction of said second bearing being in point symmetry to each other is misalignment of center of said second shaft from center of said second bearing.

13. A shaft-misalignment measuring method as described in claim 9;
wherein, in said third step, inclination of said first shaft is obtained based on dimension to a first fixed point on an upper side of said first shaft and dimension to a second fixed point on a lower side of said first shaft on a same surface with said first fixed point; and
wherein, inclination of said second shaft is obtained based on dimension to a third fixed point on an upper side of said second shaft and dimension to a fourth fixed point on a lower side of said second shaft on a same surface with said third fixed point.

14. A shaft-misalignment measuring method as described in claim 13;
wherein, where dimension between a measuring point of dimension to said first fixed point and a measuring point of dimension to said second fixed point is d1;
where dimensions to said first and second fixed points are du1 and dd1, respectively;
where dimension between a supporting point where said first shaft is supported and a connection point where said first and second shafts are connected is D1;
where dimension between a measuring point of dimension to said third fixed point and a measuring point of dimension to said fourth fixed point is d2;
where dimensions to said third and fourth fixed points are du2 and dd2, respectively;
where dimension between a supporting point where said second shaft is supported and a connecting point where said first and second shafts are connected is D2,
value of $D1 \times (du1-dd1)/d1 + D2 \times (du2-dd2)/d2$ is a part of shaft-misalignment amount of said first and second shafts.

15. A single-shaft combined plant, comprising:
a gas turbine which serves as a first body of revolution;
a steam turbine which serves as a second body of revolution;
a clutch which connects and disconnects a first shaft of said gas turbine and a second shaft of said steam turbine; and
a shaft-misalignment-measuring device comprising:
a plurality of first gap-measuring sensors which are mounted at a plurality of points in a circumferential direction of a first bearing where said first shaft is mounted;
a plurality of second gap-measuring sensors which are mounted at a plurality of points in a circumferential direction of a second bearing where said second shaft is mounted; and
a shaft-misalignment operating section which obtains misalignment of center of said first shaft from center of said first bearing based on dimensions to said first shaft from a plurality of said points in a circumferential direction of said first bearing that are measured by said first gap-measuring sensor; obtains misalignment of center of said second shaft from center of said second bearing based on dimensions to said second shaft from a plurality of said points in a circumferential direction of said second bearing that are measured by said second gap-measuring sensor; and obtains a part of shaft-misalignment amount of said first and second shafts based on misalignment of centers of said first and second shafts,
wherein, at start-up time, when said steam turbine is started up, with said first shaft and said second shaft disconnected by said clutch, after said gas turbine is started up, speed-increase ratio of rotation speed of said steam turbine is set based on shaft-misalignment amount of said first and second shafts that is measured with said shaft-misalignment-measuring device.

16. A single-shaft combined plant as described in claim 15,
wherein, the larger shaft-misalignment amount of said first and second shafts that is measured by said shaft-misalignment-measuring device is, the smaller speed-increase ratio of rotation speed of said steam turbine is made.

17. A single-shaft combined plant as described in claim 15,
wherein, said shaft-misalignment-measuring device comprises:
a first temperature sensor which measures temperature of a first bearing pedestal supporting a first bearing where said first shaft is mounted;

a second temperature sensor which measures a temperature of a second bearing pedestal supporting a second bearing where said second shaft is mounted;

a shaft-misalignment operating section which obtains expansion amount of said first bearing pedestal from temperatures that are measured by said first temperature sensor; obtains expansion amount of said second bearing pedestal from temperatures that are measured by said second temperature sensor; and obtains a part of shaft-misalignment amount of said first and second shafts based on expansion amounts of said first and second bearing pedestals.

18. A single-shaft combined plant as described in claim 15;

wherein, said shaft-misalignment-measuring device comprises:

a first gap-measuring sensor which measures dimension to a first fixed point on an upper side of said first shaft;

a second gap-measuring sensor which measures dimension to a second fixed point on a lower side of said first shaft on a same surface with said first fixed point;

a third gap-measuring sensor which measures dimension to a third fixed point on an upper side of said second shaft;

a fourth gap-measuring sensor which measures dimension to a fourth fixed point on a lower side of said second shaft on a same surface with said third fixed point; and a shaft-misalignment operating section which obtains inclination of said first shaft from dimensions to said first and second fixed points that are measured by said first and second gap-measuring sensors, respectively; obtains inclination of said second shaft from dimensions to said third and fourth fixed points that are measured by said third and fourth gap-measuring sensors, respectively; and obtains a apart of shaft-misalignment amount of said first and second shafts based on inclination of said first and second shafts.

19. A single-shaft combined plant as described in claim 15, wherein, further, speed-increase ratio of rotation speed of said steam turbine is changed based on temperature of rotor of said steam turbine.

20. A single-shaft combined plant as described in claim 19, wherein, the lower temperature of rotor of said steam turbine is, the smaller speed-increase ratio of rotation speed of said steam turbine is changed to be.

21. A single-shaft combined plant comprising:

a gas turbine which serves as a first body of revolution;

a steam turbine which serves as a second body of revolution;

a clutch which connects and disconnects a first shaft of said gas turbine and a second shaft of said steam turbine;

a shaft-misalignment measuring device comprising:

a plurality of first gap-measuring sensors which are mounted at a plurality of points in a circumferential direction of a first bearing where said first shaft is mounted:

a plurality of second gap-measuring sensors which are mounted at a plurality of points in a circumferential direction of a second bearing where said second shaft is mounted; and a shaft-misalignment operating section which obtains misalignment of center of said first shaft from center of said first bearing based on dimensions to said first shaft from a plurality of said points in a circumferential direction of said first bearing that are measured by said first gap-measuring sensor; obtains misalignment of center of said second shaft from center of said second bearing based on dimensions to said second shaft from a plurality of said points in a circumferential direction of said second bearing that are measured by said second gap-measuring sensor; and obtains a part of shaft-misalignment amount of said first and second shafts based on misalignment of centers of said first and second shafts, wherein, at start-up time, when said steam turbine is started up, with said first shaft and second shaft disconnected by said clutch, after said gas turbine is started-up, heat soak time of said steam turbine is set based on shaft-misalignment amount of said first and second shafts that is measured by said shaft-misalignment-measuring device.

22. A single-shaft combined plant as described in claim 21, wherein, the larger shaft-misalignment amount of said first and second shafts that is measured by said shaft-misalignment-measuring device is, the longer heat soak time of said steam turbine is made.

23. A single-shaft combined plant as described in claim 21, wherein, said shaft-misalignment-measuring device comprises:

a first temperature sensor which measures temperature of a first bearing pedestal supporting a first bearing where said first shaft is mounted;

a second temperature sensor which measures temperature of a second bearing pedestal supporting a second bearing where said second shaft revolution is mounted; and a shaft-misalignment operating section which obtains expansion amount of said first bearing pedestal from temperatures measured by said first temperature sensor; obtains expansion amount of said second bearing pedestal from temperatures measured by said second temperature sensor; and obtains a part of shaft-misalignment amount of said first and second shafts based on expansion amounts of said first and second bearing pedestals.

24. A single-shaft combined plant described as in claim 21, wherein, said shaft-misalignment-measuring device comprises:

a first gap-measuring sensor which measures dimension to a first fixed point on an upper side of said first shaft;

a second gap-measuring sensor which measures dimension to a second fixed point on a lower side of said first shaft on a same surface with said first fixed point;

a third gap-measuring sensor which measures dimension to a third fixed point on an upper side of said second shaft;

a fourth gap-measuring sensor which measures dimension to a fourth fixed point on a lower side of said second shaft on a same surface with said third fixed point; and a shaft-misalignment operating section which obtains inclination of said first shaft from dimensions to said first and second fixed points that are measured by said first and second gap-measuring sensors, respectively; obtains inclination of said second shaft from dimensions to said third and fourth fixed points that are measured by said third and fourth gap-measuring sensors, respectively; and obtains a apart of shaft-misalignment amount of said first and second shafts based on inclination of said first and second shafts.

25. A single-shaft combined plant as described in claim 21, wherein, further, heat soak time of said steam turbine is changed based on temperature of rotor of said steam turbine.

26. A single-shaft combined plant as described in claim 25, wherein, the lower temperature of rotor of said steam turbine is, the longer heat soak time of said steam turbine is changed to be.

27. A single-shaft combined plant as described in claim 21, wherein, at start-up time when said steam turbine is started up after said gas turbine is started up, speed-increase ratio of rotation speed of said steam turbine is further set based on shaft-misalignment amount of said first and second shafts that is measured by said shaft-misalignment-measuring device.

28. A single-shaft combined plant as described in claim 27, wherein, the larger shaft-misalignment amount of said first and second shafts measured by said shaft-misalignment-measuring device is, the smaller speed-increase ratio of rotation speed of said steam turbine is made.

29. A single-shaft combined plant as described in claim 27, wherein, further, speed-increase ratio of rotation speed of said steam turbine is changed based on temperature of rotor of said steam turbine.

30. A single-shaft combined plant as described in claim 29, wherein, the lower temperature of rotor of said steam turbine is, the smaller speed-increase ratio of rotation speed of said steam turbine is changed to be.

* * * * *